United States Patent
King

(10) Patent No.: US 11,938,084 B2
(45) Date of Patent: Mar. 26, 2024

(54) EXTERNAL DEFIBRILLATOR PADS WITH VISUAL CPR FEEDBACK INDICATOR

(71) Applicant: KONINKLIJKE PHILIPS N.V., Eindhoven (NL)

(72) Inventor: Martin J. King, Seattle, WA (US)

(73) Assignee: Koninklijke Philips N.V., Eindhoven (NL)

( * ) Notice: Subject to any disclaimer, the term of this patent is extended or adjusted under 35 U.S.C. 154(b) by 737 days.

(21) Appl. No.: 17/074,219

(22) Filed: Oct. 19, 2020

(65) Prior Publication Data

US 2022/0117838 A1  Apr. 21, 2022

(51) Int. Cl.
| | | |
|---|---|---|
| *A61H 31/00* | (2006.01) | |
| *A61N 1/04* | (2006.01) | |
| *A61N 1/39* | (2006.01) | |
| *A61B 5/259* | (2021.01) | |
| *A61B 5/339* | (2021.01) | |

(52) U.S. Cl.
CPC .......... *A61H 31/005* (2013.01); *A61N 1/046* (2013.01); *A61N 1/0492* (2013.01); *A61N 1/39044* (2017.08); *A61N 1/3993* (2013.01); *A61B 5/259* (2021.01); *A61B 5/339* (2021.01); *A61H 2201/5043* (2013.01); *A61H 2201/5084* (2013.01)

(58) Field of Classification Search
CPC ...... A61H 31/005; A61H 31/007; A61N 1/39; A61N 1/3904; A61N 1/39044
See application file for complete search history.

(56) References Cited

U.S. PATENT DOCUMENTS

| | | | |
|---|---|---|---|
| 6,587,726 B2 * | 7/2003 | Lurie | A61N 1/3601 |
| | | | 607/42 |
| 9,358,178 B1 * | 6/2016 | Morgan | A61H 31/005 |
| 9,585,603 B2 | 3/2017 | Centen | |
| 10,406,345 B2 | 9/2019 | Silver | |

(Continued)

FOREIGN PATENT DOCUMENTS

| | | | | |
|---|---|---|---|---|
| CA | 2615272 A1 * | 6/2008 | ............ | A61H 31/00 |
| WO | WO-0170332 A2 * | 9/2001 | ............ | A61H 31/00 |

(Continued)

OTHER PUBLICATIONS

International Search Report for PCT/EP2021/078264 filed Oct. 13, 2021.

*Primary Examiner* — Michael J Tsai

(57) ABSTRACT

An automated external defibrillator (210) for use during CPR comprising: a first electrode pad (370a) configured to obtain an electrocardiogram (ECG) signal from an individual; a second electrode pad (370b) configured to obtain ECG signal from the individual, wherein the first and/or the second electrode pad comprises an electrode pad visual display (372) configured to be visible while providing CPR to the individual; a controller (310) configured to: (i) process an electrical and/or an accelerometer signal to determine a depth of one or more chest compressions during CPR; (ii) compare the determined depth of the chest compressions to a threshold depth; (ii) determine, based on the comparison, that the determined depth exceeds or falls below the threshold depth; and (iii) direct the electrode pad visual display to provide a depth indication to the user that the determined depth of the chest compressions exceeds or falls below the threshold depth.

13 Claims, 7 Drawing Sheets

(56) References Cited

U.S. PATENT DOCUMENTS

| | | | |
|---|---|---|---|
| 10,433,767 B2* | 10/2019 | Richard | A61B 5/7455 |
| 10,780,020 B2 | 9/2020 | Hunt | |
| 2002/0188332 A1* | 12/2002 | Lurie | A61N 1/39044 |
| | | | 607/48 |
| 2004/0082888 A1* | 4/2004 | Palazzolo | A61B 5/7242 |
| | | | 601/41 |
| 2004/0215244 A1* | 10/2004 | Marcovecchio | A61B 5/0205 |
| | | | 607/5 |
| 2005/0131465 A1* | 6/2005 | Freeman | A61N 1/3993 |
| | | | 607/5 |
| 2006/0270952 A1* | 11/2006 | Freeman | A61H 31/005 |
| | | | 601/41 |
| 2008/0146973 A1* | 6/2008 | Lund | A61H 31/005 |
| | | | 601/40 |
| 2008/0171311 A1* | 7/2008 | Centen | A61H 31/005 |
| | | | 601/41 |
| 2008/0312565 A1* | 12/2008 | Celik-Butler | G09B 23/288 |
| | | | 73/488 |
| 2010/0234908 A1 | 9/2010 | Didon | |
| 2011/0201979 A1* | 8/2011 | Voss | A61H 31/004 |
| | | | 601/41 |
| 2011/0202100 A1* | 8/2011 | Tan | G16H 20/30 |
| | | | 607/6 |
| 2012/0330200 A1* | 12/2012 | Voss | A61H 31/004 |
| | | | 601/41 |
| 2013/0023781 A1* | 1/2013 | Freeman | A61B 5/0816 |
| | | | 601/41 |
| 2013/0310718 A1* | 11/2013 | Jensen | A61H 31/005 |
| | | | 601/41 |
| 2014/0039359 A1* | 2/2014 | Madanat | A61H 31/005 |
| | | | 601/15 |
| 2014/0257150 A1* | 9/2014 | Totman | A61H 31/007 |
| | | | 601/41 |
| 2015/0045704 A1* | 2/2015 | Lurie | A61M 16/0048 |
| | | | 601/41 |
| 2015/0094625 A1* | 4/2015 | Freeman | A61H 31/00 |
| | | | 601/41 |
| 2017/0106183 A1* | 4/2017 | Silver | A61H 31/005 |
| 2018/0342178 A1* | 11/2018 | Gold | A61H 31/004 |
| 2019/0255340 A1 | 8/2019 | Freeman | |

FOREIGN PATENT DOCUMENTS

| | | | |
|---|---|---|---|
| WO | 20061-4977 A2 | 10/2006 | |
| WO | WO-2007057825 A2 * | 5/2007 | A61B 5/6822 |

* cited by examiner

EXTERNAL DEFIBRILLATOR PADS WITH VISUAL CPR FEEDBACK INDICATOR

FIELD OF THE INVENTION

The present disclosure is directed generally to systems and methods for providing visual feedback during CPR via external defibrillator electrode pads.

BACKGROUND

Cardiopulmonary resuscitation (CPR) is used to artificially circulate blood, and thus oxygen, through the body of a person who has suffered a cardiac incident until they have a shockable heart rhythm on which a defibrillator can be used, or other medical care can be provided at a hospital or trauma center. The quality of the CPR administered, such as the depth and rate of chest compressions, can vary based on a number of factors such as experience of the rescuer, fatigue, and many other factors. However, quality CPR is essential to survival of the person.

Currently, a number of devices exist that can provide feedback to the user about the quality of the CPR being administered. One example of these devices are automated external defibrillator (AED) devices which deliver a high-voltage shock to the heart in order to restore normal sinus rhythm in people who are experiencing arrhythmia, such as ventricular fibrillation or ventricular tachycardia AEDs automatically analyze the electrocardiogram (ECG) rhythm to determine whether defibrillation is warranted and necessary. After deciding that a shock is appropriate and necessary, the AED charges itself to deliver the high-voltage shock, and then instructs the user to press a button causing the device to deliver the defibrillation shock. Many AED devices incorporate sensors which can detect the applied force, depth, and/or rate of chest compressions during CPR.

Other devices configured to provide feedback to the user about the quality of the CPR being administered include devices that are placed directly on the patient's chest under the rescuer's hands during CPR. The device includes sensors which can detect the applied force, depth, and/or rate of chest compressions during CPR, and can provide feedback to the user.

However, these existing devices and methods have significant drawbacks that can affect the quality and application of CPR during an emergency event. As just one example, most devices provide audible instructions or feedback to a user, which can be difficult or impossible to hear and/or comprehend during noisy and stressful emergency situations. Further, supplemental devices that are used on the chest under the hands are extra accessories that need to be available, cleaned, and maintained, and can waste valuable recovery time during application of the device to the chest.

SUMMARY OF THE INVENTION

Accordingly, there is a continued need in the art for AED devices that provide visual chest compression depth and/or rate feedback during CPR administration.

The present disclosure is directed to inventive methods and systems for an automated external defibrillator device for use during cardiopulmonary resuscitation. Various embodiments and implementations herein are directed to a system comprising a first electrode pad configured to obtain at least a portion of an electrocardiogram (ECG) signal from an individual, and a second electrode pad configured to obtain at least a portion of an electrocardiogram (ECG) signal from the individual. The first electrode pad and/or the second electrode pad comprises an electrode pad visual display configured to be visible to a user of the AED while providing CPR to the individual. The device also comprises a controller that processes an electrical signal and/or an accelerometer signal received from a sensor to determine a depth of one or more chest compressions during CPR, and compares the determined depth to a threshold depth. If the determined depth exceeds or falls below the threshold depth, the controller directs the electrode pad visual display to provide a depth indication to the user of the AED that the determined depth of the one or more chest compressions during CPR exceeds or falls below the threshold depth. The controller can perform the same functions to monitor a rate of chest compressions.

Generally, in one aspect, an automated external defibrillator (AED) for use during cardiopulmonary resuscitation (CPR) is provided. The device includes: a first electrode pad configured to obtain at least a portion of an electrocardiogram (ECG) signal from an individual; a second electrode pad configured to obtain at least a portion of an electrocardiogram (ECG) signal from the individual, wherein the first electrode pad and/or the second electrode pad comprises an electrode pad visual display configured to be visible to a user of the AED while providing CPR to the individual; a controller in communication with the first electrode pad and the second electrode pad, the controller configured to: (i) process an electrical signal and/or an accelerometer signal received from a sensor to determine a depth of one or more chest compressions during CPR; (ii) compare the determined depth of the one or more chest compressions during CPR to a threshold depth; (ii) determine, based on the comparison, that the determined depth exceeds or falls below the threshold depth; and (iii) direct the electrode pad visual display to provide a depth indication to the user of the AED that the determined depth of the one or more chest compressions during CPR exceeds or falls below the threshold depth.

According to an embodiment, the controller is further configured to: (i) process an electrical signal and/or an accelerometer signal received from a sensor to determine a rate of chest compressions during CPR; (ii) compare the determined rate of the chest compressions during CPR to a threshold rate; (ii) determine, based on the comparison, that the determined rate exceeds or falls below the threshold rate; and (iii) direct the electrode pad visual display to provide a rate indication to the user of the AED that the determined rare of the chest compressions during CPR exceeds or falls below the threshold rate.

According to an embodiment, the sensor comprises an accelerometer in the first electrode pad and/or in the second electrode pad.

According to an embodiment, the first electrode pad and/or in the second electrode pad is disposable.

According to an embodiment, the electrode pad visual display comprises one or more LEDs configured to provide the indication to the user of the AED that the determined depth of the one or more chest compressions during CPR exceeds or falls below the threshold depth.

According to an embodiment, the electrode pad visual display is configured to provide the depth indication via one or more colors, one or more words, and/or one or more icons.

According to an embodiment, the electrode pad visual display is configured to provide the rate indication via one or more colors, one or more words, and/or one or more icons.

According to an embodiment, the electrode pad visual display is configured to provide the rate indication via a light, and wherein the controller is configured to: (i) initially direct the light to flash at the determined rate; (ii) subsequently direct the light to flash at a rate closer to the threshold rate.

According to an embodiment, both the first electrode pad and the second electrode pad comprise an electrode pad visual display.

According to another aspect is a method for cardiopulmonary resuscitation (CPR) using an automated external defibrillator (AED). The method includes: (i) processing an electrical signal and/or an accelerometer signal received from a sensor to determine a depth of one or more chest compressions during CPR; (ii) comparing the determined depth of the one or more chest compressions during CPR to a threshold depth; (iii) determining, based on the comparison, that the determined depth exceeds or falls below the threshold depth; and (iv) providing, via the electrode pad visual display, a depth indication to the user of the AED that the determined depth of the one or more chest compressions during CPR exceeds or falls below the threshold depth.

According to an embodiment, the method further includes: (i) processing an electrical signal and/or an accelerometer signal received from a sensor to determine a rate of chest compressions during CPR; (ii) comparing the determined rate of the chest compressions during CPR to a threshold rate; (iii) determining, based on the comparison, that the determined rate exceeds or falls below the threshold rate; and (iv) providing, via the electrode pad visual display, a rate indication to the user of the AED that the determined rare of the chest compressions during CPR exceeds or falls below the threshold rate.

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

In one network implementation, one or more devices coupled to a network may serve as a controller for one or more other devices coupled to the network (e.g., in a master/slave relationship). In another implementation, a networked environment may include one or more dedicated controllers that are configured to control one or more of the devices coupled to the network. Generally, multiple devices coupled to the network each may have access to data that is present on the communications medium or media; however, a given device may be "addressable" in that it is configured to selectively exchange data with (i.e., receive data from and/or transmit data to) the network, based, for example, on one or more particular identifiers (e.g., "addresses") assigned to it.

The term "network" as used herein refers to any interconnection of two or more devices (including controllers or processors) that facilitates the transport of information (e.g. for device control, data storage, data exchange, etc.) between any two or more devices and/or among multiple devices coupled to the network. As should be readily appreciated, various implementations of networks suitable for interconnecting multiple devices may include any of a variety of network topologies and employ any of a variety of communication protocols. Additionally, in various networks according to the present disclosure, any one connection between two devices may represent a dedicated connection between the two systems, or alternatively a non-dedicated connection. In addition to carrying information intended for the two devices, such a non-dedicated connection may carry information not necessarily intended for either of the two devices (e.g., an open network connection). Furthermore, it should be readily appreciated that various networks of devices as discussed herein may employ one or more wireless, wire/cable, and/or fiber optic links to facilitate information transport throughout the network.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of an automated external defibrillator configured to provide chest compression depth and/or rate feedback to a user. More generally, Applicant has recognized that it would be beneficial to provide an automated external defibrillator configured to provide visual feedback to a user. In view of the foregoing, various embodiments and implementations are directed to an automated external defibrillator device comprising a first electrode pad configured to obtain at least a portion of an electrocardiogram (ECG) signal from an individual, and a second electrode pad configured to obtain at least a portion of an electrocardiogram (ECG) signal from the individual. According to an embodiment, the first electrode pad and/or the second electrode pad is further configured to obtain one or more additional signals such as an impedance signal, among other possible signals. The first electrode pad and/or the second electrode pad comprises an electrode pad visual display configured to be visible to a user of the AED while providing CPR to the individual. The device also comprises a controller that processes an electrical signal and/or an accelerometer signal received from a sensor to determine a depth of one or more chest compressions during CPR, and compares the determined depth to a threshold depth. If the determined depth exceeds or falls below the threshold depth, the controller directs the electrode pad visual display to provide a depth indication to the user of the AED that the determined depth of the one or more chest compressions during CPR exceeds or falls below the threshold depth. The controller can perform the same functions to monitor a rate of chest compressions.

The inventive aspects described or otherwise envisioned herein will save human lives. Inefficient CPR leads to thousands of preventable deaths every year, even when AED devices are available. The use of one or more electrode pad visual displays configured to be visible to a user of an AED while providing CPR to a victim provides numerous life-saving benefits. Among those benefits is the ability to receive direction for chest compression depth and/or rate even if the person providing CPR is deaf or hard of hearing. Similarly, given the problematic background noise levels that may exist at an emergency scene, providing an electrode pad visual display for depth and/or rate indications leads to better chest compression depth and rate and thus saves human lives.

Figure 1:
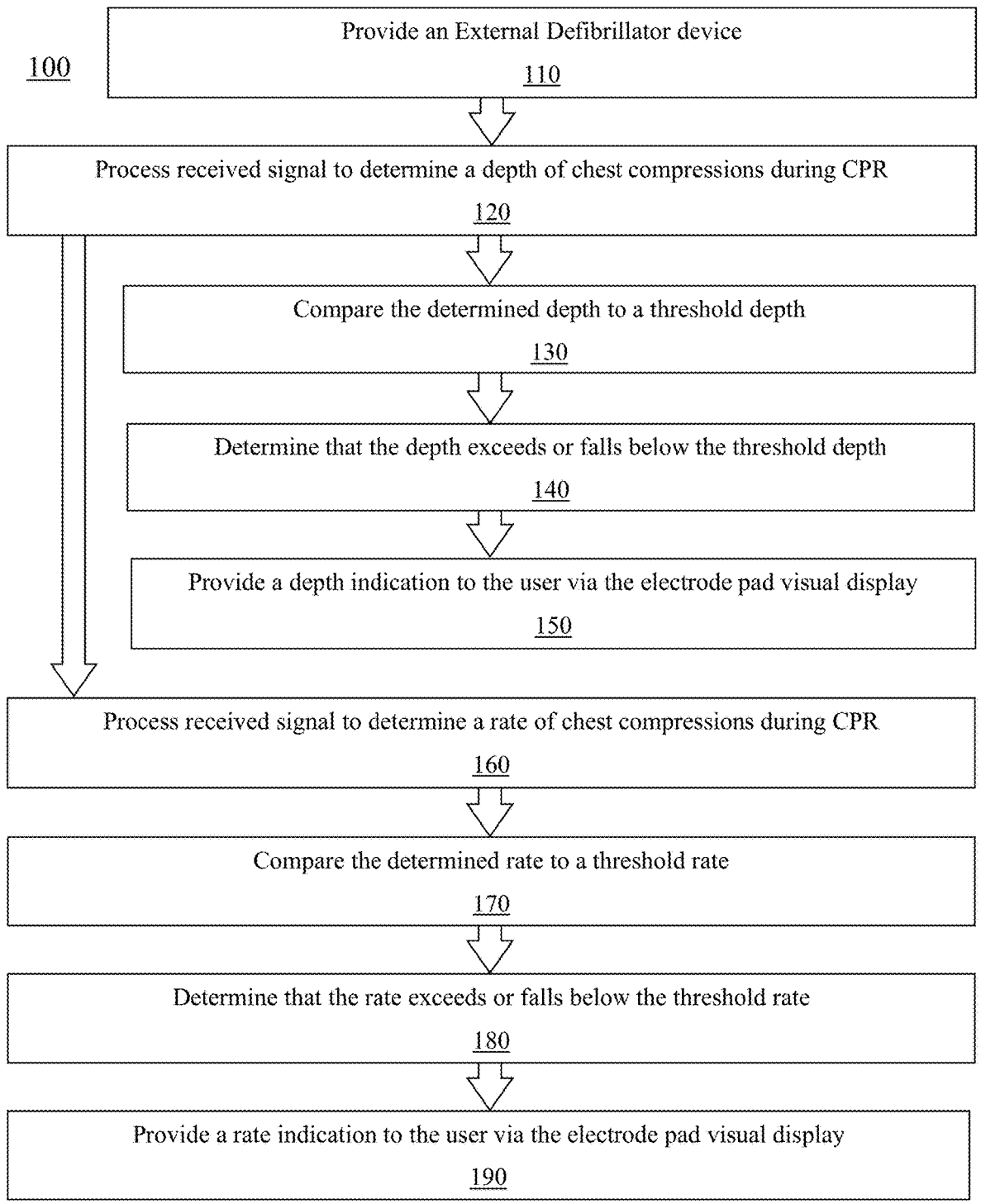
FIG. 1 is a flowchart of a method for providing visual chest compression depth and/or rate feedback during CPR administration, in accordance with an embodiment.

Referring to FIG. 1, in accordance with an embodiment, is a flowchart of a method 100 for cardiopulmonary resuscitation (CPR) using an automated external defibrillator (AED). At step 110 of the method, an AED is provided. The AED can be any of the systems described or otherwise envisioned herein. As described or otherwise envisioned herein, the AED can be a permanent installation or can be a portable device.

Figure 2:
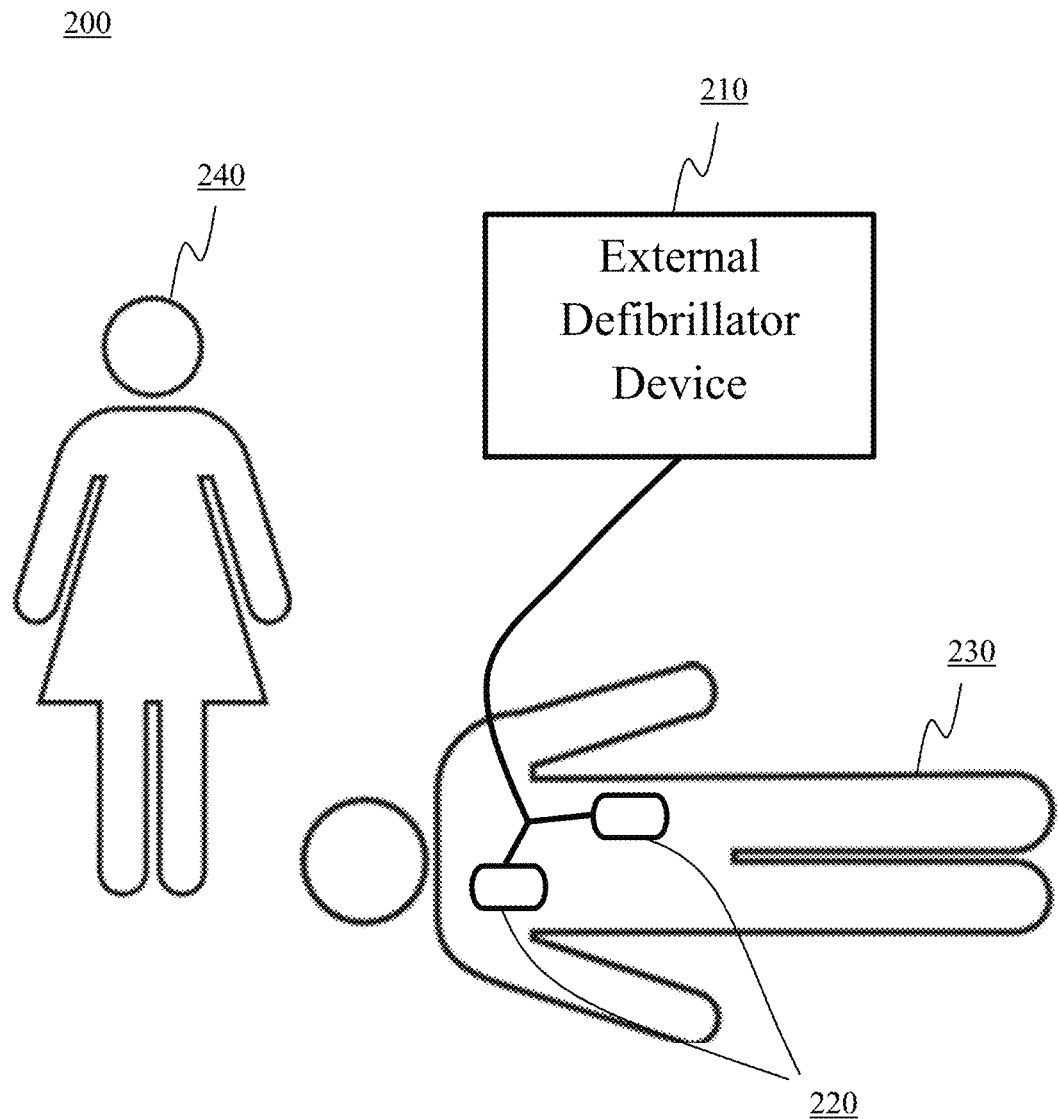
FIG. 2 is a schematic representation of an emergency situation requiring CPR and the use of an AED device, in accordance with an embodiment.

Referring to FIG. 2, in accordance with an embodiment, is a schematic representation of an emergency situation requiring CPR and optionally the use of an AED device 210. Victim 230 is suffering from a cardiac event such as cardiac arrest, and a responder 240 is using the AED device and administering CPR to provide support. The AED device 210 includes first and second electrode pads 220 configured to detect an electrocardiogram (ECG) signal from the victim and further configured to provide, if warranted and necessary, a high-voltage shock to the victim.

Figure 3:
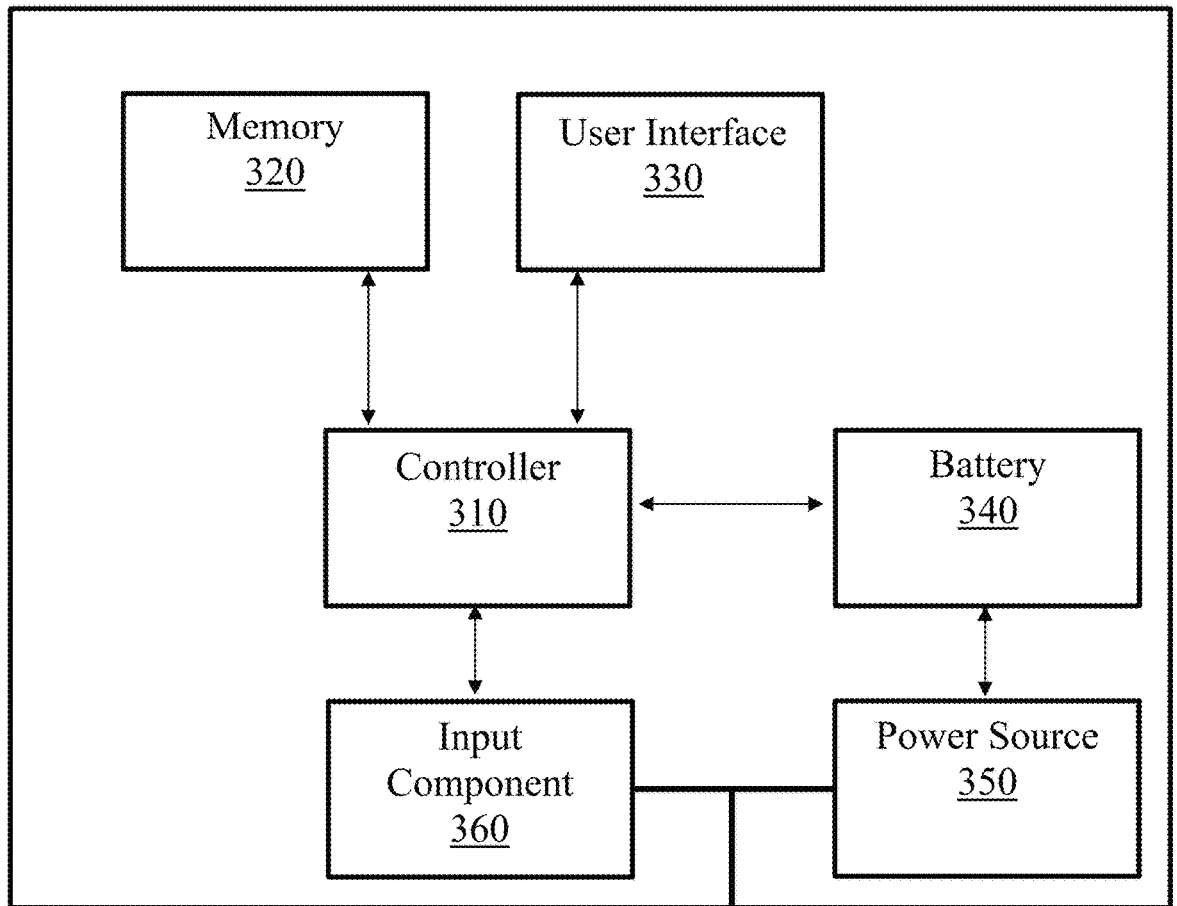
FIG. 3 is a schematic representation of an AED device, in accordance with an embodiment.
Figure 3:
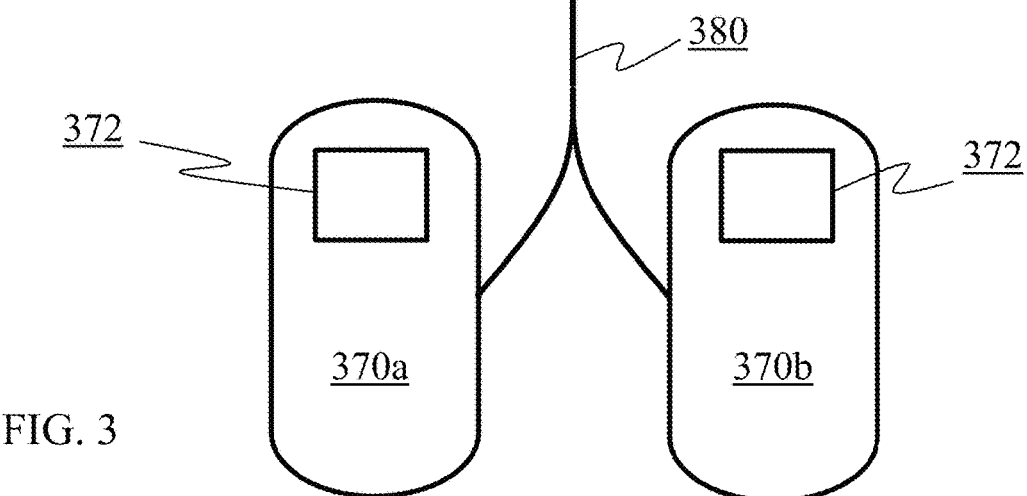

Referring to FIG. 3, in accordance with an embodiment, is a schematic representation of an AED device 200. The AED device may be any of the devices or systems described or otherwise envisioned herein. According to embodiment, the AED device comprises one or more of a controller 310, a memory 320, a user interface 330, a battery 340, a power source 350, an input component 360, and/or first and second electrode pads 370a,b. The electrode pads are connected by a lead 380 to one or more of the input component and the power source, and one or both comprises an electrode pad visual display 372.

According to embodiment, the user interface 330 of the AED device is configured for use in connection with and/or during an emergency situation, as discussed further herein. For example, user interface 330 can comprise a graphical user interface configured to provide instructions to a user during an emergency. User interface 330 may comprise an input/output device, a haptic device, a touch screen, an optical display, a microphone, a keypad, a keyboard, a pointing device, an image capture device, a video camera, an audio output device, or any combination thereof.

The input component 360 may be the controller or a separate component. The input component is configured to receive input from the first and second electrode pads 370a,b, such as electrical signals obtained by the pads. For example, the pads can be configured to obtain an electrocardiogram signal, and/or an impedance or other signal, from the victim 230 when the pads are placed on the victim's chest. The input component may analyze or process or pre-process the received input, or the input component may pass the received input to the controller or other component of the AED The controller 310 is operatively coupled to memory 320, user interface 330, input component 260, battery 340, and/or power source 350. The controller 310 is capable of executing instructions stored in memory 320 or other data storage or otherwise processing data to, for example, perform one or more steps of the method. Controller 310 may be formed of one or multiple modules. The Processor or Controller 310 may take any suitable form, including but not limited to a microprocessor, microcontroller, multiple microcontrollers, circuitry, field programmable gate array (FPGA), application-specific integrated circuit (ASIC), a single processor, or plural processors.

Memory 320 can take any suitable form, including a non-volatile memory and/or RAM. The memory 320 may include various memories such as, for example L1, L2, or L3 cache or system memory. As such, the memory 320 may include static random access memory (SRAM), dynamic RAM (DRAM), flash memory, read only memory (ROM), or other similar memory devices. The memory can store, among other things, an operating system. The RAM is used by the processor for the temporary storage of data. According to an embodiment, an operating system may contain code which, when executed by the processor, controls operation of one or more components of the device. It will be apparent that, in embodiments where the processor implements one or more of the functions described herein in hardware, the software described as corresponding to such functionality in other embodiments may be omitted.

While device 210 is shown as including one of each described component, the various components may be duplicated in various embodiments. For example, controller 310 may include multiple microprocessors that are configured to independently execute the methods described herein or are configured to perform steps or subroutines of the methods described herein such that the multiple processors cooperate to achieve the functionality described herein. Further, where one or more components of device 210 is implemented in a cloud computing system, the various hardware components may belong to separate physical systems. For example, controller 310 may include a first processor in a first server and a second processor in a second server. Many other variations and configurations are possible.

The battery 340 can comprise any suitable power source or power supply for the AED device. Power source 350, which may be a component of battery 340, is similarly any suitable power source or power supply for the AED device. For example, power source 350 can comprise a high voltage capacitor configured to store energy for defibrillating shocks, where the capacitor is charged by battery 340.

The AED device 210 further comprises a first electrode pad 370a and a second electrode pad 370b. The electrode pads are operatively coupled to power source 350 via lead 380 and are configured to provide an electrical shock during use of the AED device. According to an embodiment, the first electrode pad 370a and the second electrode pad 370b are disposable. Thus, after use in an emergency situation, the pads can be disposed of and replaced with new pads. Additionally, the pads may have a predicted lifetime with an expiration date, such that upon expiration the pads can be disposed of and replaced with new pads.

According to an embodiment, the AED device is configured to be activated by a user in an emergency situation, such as when a victim or potential victim is believed to be suffering from a cardiac incident. The AED device may be activated by user input, such as by a touch or voice command. In response to being activated, the AED device provides visual and/or audible instructions to the user, including but not limited to instructions regarding placement of the first electrode pad 370a and a second electrode pad 370b on the victim's chest, administration of CPR, beginning and pausing CPR, warning of an impending shock, administration of a shock, and other instructions.

According to an embodiment, the AED device is configured to receive an input from the first electrode pad 370a and the second electrode pad 370b. For defibrillation purposes, the AED device is configured to receive a signal indicating an electrocardiogram of the victim. The AED device comprises an algorithm configured to receive the signal and analyze the signal to determine if the ECG signal of the victim is suitable for administration of a shock via the first electrode pad 370a and/or the second electrode pad 370b. In some cases, the signal will indicate that a shock would not be beneficial or advantageous. In other cases, the signal will indicate that a shock will be beneficial and/or advantageous. In the latter case, the controller will direct the battery to charge the power source to provide a high-voltage shock to the victim via the first electrode pad 370a and/or the second electrode pad 370b.

Returning to method 100 in FIG. 1, at step 120 of the method the system receives and processes a signal received from a sensor to determine a depth of one or more chest compressions during CPR. According to an embodiment, the signal is an electrical signal and/or an accelerometer signal, although other types of sensor signals are possible. The signal is optionally detected by a sensor in the AED device, a sensor in one or both of the electrode pads, or from some other source. The signal is a mechanical and/or electrical signal that can be analyzed or processed to determine a depth of one or more chest compressions during CPR. According to an embodiment, impedance signals between the two or more electrode pads can be used to detect CPR-related impedance changes, including depth and/or rate of CPR compressions. According to another embodiment, the chest electrode signals are analyzed to separate cardiac-related signals (e.g., electrocardiogram or ECG) and a CPR-related artifacts such as depth and/or rate of CPR compressions. Many other methods are possible to analyze the mechanical and/or electrical signal detected by the AED device sensor to determine or estimate a depth of one or more chest compressions during CPR.

According to an embodiment, the system is configured to analyze the signal after one chest compression or multiple chest compressions, above or below a certain threshold. The signal can be stored in memory while being stored or after being processed. Accordingly, the determined depth can be stored in memory during or after processing.

According to an embodiment, the determined depth may be a numerical value, percentage, or other value indicating a depth. For example, the determined depth may be a measurement in inches or centimeters. Therefore, the output of step 120 of the method may be any indication of determined depth, such as 3 inches (7.62 cm), 2 inches (5.08 cm), 1 inch (2.54 cm), or any other measurement.

At step 130 of the method, the AED device compares the determined depth of the one or more chest compressions during CPR to a threshold depth. The threshold depth can be any depth determined to be sufficient to compress the victim's chest and heart in order to push blood throughout the victim's body. This depth can be determined experimentally, can be based on CPR standards, or otherwise determined. According to current standards from the American Heart Association, for example, users should provide chest compressions at a rate of 100 to 120 compressions/minute to a depth of at least 2 inches (5 cm) for an average depth. However, users should avoid excessive chest compression depths greater than 2.4 inches (6 cm).

For example, the threshold depth may be determined or based, in whole or in part, on a parameter of the victim. For example, the threshold depth may be deeper for victims with larger chests or larger chest circumference, and may be shallower for victims with smaller chests or smaller chest circumference. The victim's chest size or circumference may be determined or based on a wide variety of factors, including in whole or in part on a mechanical and/or electrical signal detected by the AED device sensor. For example, the distance between the first electrode pad and the second electrode pad can be determined by a signal passed between them or a signal differentially detected by them. If the first and second electrode pads are properly placed, that determined distance can be utilized to calculate the victim's chest circumference. The determined or calculated chest circumference can be used to determine or adjust the threshold depth necessary to perform adequate CPR. The victim's body fat percentage, which might also be determined from the mechanical and/or electrical signal detected by the AED device sensor, can also be factored into the calculation or determination of the victim's chest circumference and thus the threshold depth.

According to an embodiment, the threshold depth is pre-programmed into the AED device, such as into the controller, during manufacture or during installation. For example, if the AED device is known to be utilized for adults, an adult threshold depth may be programmed into the AED device. If the AED device is known to be utilized for children, a child threshold depth may be programmed into the AED device. Alternatively, the threshold depth may be a setting that can be adjusted by the user during installation or before/during use of the AED device in an emergency situation.

At step 140 of the method, the AED device determines, based on the comparison, that the determined depth exceeds or falls below the threshold depth. According to an embodiment, the result of the comparison of the determined depth of the one or more chest compressions to the predetermined threshold depth can be a numerical value or simply a digital "exceeds" or "falls below" indication. There are many other ways to indicate that the determined depth exceeds or falls below the threshold depth.

For example, the comparison may result in a numerical value indicating by how much the determined depth exceeds or falls below the threshold depth. The numerical value may be a distance, a percentage, or any other value indicating the difference between the determined depth and the threshold depth. For example, as described above, possible determined depth measurements may be measurements such as 3 inches (7.62 cm), 2 inches (5.08 cm), 1 inch (2.54 cm), among many other possible measurements or indications of determined depth. Similarly, the threshold depth for an adult may be within the range of 2 inches (5.08 cm) to 2.4 inches (6.10 cm). Accordingly, the three example measurements result in the following comparisons:

1. A determined depth of 3 inches (7.62 cm) compared to the threshold depth range of 2 inches (5.08 cm) to 2.4 inches (6.096 cm) results in a difference of between 1 and 0.6 inches (2.54 to 1.52 cm) in excess of the threshold depth. In this example, the output of step 140 of the method is a determination by the AED device that the determined depth EXCEEDS the threshold depth. In this example, the user is compressing the chest too much, which can result in serious injury and/or ineffective CPR.

2. A determined depth of 2 inches (5.08 cm) compared to the threshold depth range of 2 inches (5.08 cm) to 2.4 inches (6.096 cm) results in the determined depth falling within the threshold depth range. In this example, the output of step 140 of the method is a determination by the AED device that the determined depth neither exceeds for falls below the threshold depth.

3. A determined depth of 1 inch (2.54 cm) compared to the threshold depth range of 2 inches (5.08 cm) to 2.4 inches (6.096 cm) results in a difference of between 1 and 1.4 inches (3.56 cm) BELOW the threshold depth. In this example, the output of step 140 of the method is a determination by the AED device that the determined depth FALLS BELOW the threshold depth. In this example, the user is compressing the chest too little, which can result in ineffective CPR.

Although the previous examples are shown using exact depth measurements, it should be appreciated that these are provided only as non-limiting examples. Many other methods for comparing a determined depth to a threshold depth are possible.

At step 150 of the method, the AED devices provides, via the electrode pad visual display, a depth indication to the user of the AED that the determined depth of the one or more chest compressions during CPR exceeds or falls below the threshold depth. For example, referring to FIG. 3 are first electrode pad 370*a* and second electrode pad 370*b*. One or both of the electrode pads may comprise one or more electrode pad visual displays 372. Although FIG. 3 shows both electrode pads comprising an electrode pad visual display 372, it should be appreciated that only one pad may comprise a visual display.

According to an embodiment, the controller directs the electrode pad visual display to provide depth indication to the user of the AED that the determined depth of the one or more chest compressions during CPR exceeds or falls below the threshold depth, based on the output of step 140 of the method. Returning to the non-limiting examples discussed above, the controller may take the following action in response to each of the three comparisons:

1. A determined depth of 3 inches (7.62 cm) compared to the threshold depth range of 2 inches (5.08 cm) to 2.4 inches (6.096 cm) results in a difference of between 1 and 0.6 inches (2.54 to 1.52 cm) in excess of the threshold depth. In this example, the output of step 140 of the method is a determination by the AED device that the determined depth EXCEEDS the threshold depth. In this example, the controller directs the one or more electrode pad visual displays to provide an indication that the determined depth EXCEEDS the threshold depth.

2. A determined depth of 2 inches (5.08 cm) compared to the threshold depth range of 2 inches (5.08 cm) to 2.4 inches (6.096 cm) results in the determined depth falling within the threshold depth range. In this example, the output of step 140 of the method is a determination by the AED device that the determined depth neither exceeds for falls below the threshold depth. In this example, the controller may provide no direction to the one or more electrode pad visual displays. Alternatively, the controller may direct the one or more electrode pad visual displays to provide an indication that the determined depth is within or otherwise satisfies the threshold depth.

3. A determined depth of 1 inch (2.54 cm) compared to the threshold depth range of 2 inches (5.08 cm) to 2.4 inches (6.096 cm) results in a difference of between 1 and 1.4 inches (3.56 cm) BELOW the threshold depth. In this example, the output of step 140 of the method is a determination by the AED device that the determined depth FALLS BELOW the threshold depth. In this example, the controller directs the one or more electrode pad visual displays to provide an indication that the determined depth FALLS BELOW the threshold depth.

The indication that the determined depth exceeds or falls below the threshold depth may be any indication, provided visually by the one or more electrode pad visual displays, sufficient to communicate this information to the user. Although several examples of indications provided via the one or more electrode pad visual displays are provided below, it should be understood that these are non-limiting examples.

Figure 4A:
FIG. 4A is a schematic representation of an electrode pad visual display of an AED device, in accordance with an embodiment.
Figure 4B:
FIG. 4B is a schematic representation of an electrode pad visual display of an AED device, in accordance with an embodiment.
Figure 4C:
FIG. 4C is a schematic representation of an electrode pad visual display of an AED device, in accordance with an embodiment.

According to one embodiment, the one or more electrode pad visual displays may comprise a visual display such as a liquid crystal display or other graphical user interface configured to provide the indication regarding the determined depth. Referring to FIGS. 4A-4C, for example, the controller and/or the one or more electrode pad visual displays may be configured to activate, display, highlight, or otherwise activate or provide an indicator such as a word. In FIG. 4A, the electrode pad visual display is directed to display the phrase "TOO DEEP" because the determined depth is deeper than the threshold depth. In FIG. 4B, the electrode pad visual display is directed to display the phrase "GOOD" because the determined depth satisfies or falls within the threshold depth. In FIG. 4C, the electrode pad visual display is directed to display the phrase "TOO SHALLOW" because the determined depth is shallower than the threshold depth.

Alternatively, the one or more electrode pad visual displays may comprise LEDs that backlight the words or other indicators. For example, the LED backlighting a word such as "TOO DEEP" may be activated when the determined depth is deeper than the threshold depth. The LED backlighting a word such as "TOO SHALLOW" may be activated when the determined depth is shallower than the threshold depth.

Figure 5A:
FIG. 5A is a schematic representation of an electrode pad visual display of an AED device, in accordance with an embodiment.
Figure 5B:
FIG. 5B is a schematic representation of an electrode pad visual display of an AED device, in accordance with an embodiment.
Figure 5C:
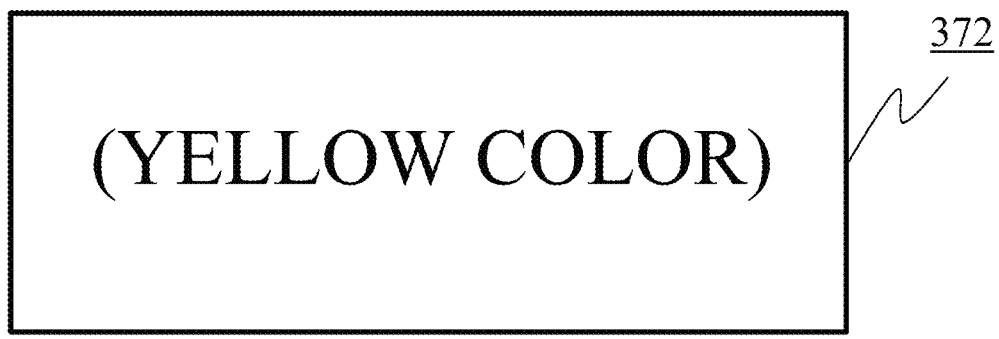
FIG. 5C is a schematic representation of an electrode pad visual display of an AED device, in accordance with an embodiment.

Referring to FIGS. 5A-5C, for example, the controller and/or the one or more electrode pad visual displays may be configured to activate, display, highlight, or otherwise activate an LED light to provide the indicator. In FIG. 5A, the electrode pad visual display is directed to activate an LED to emit red light because the determined depth is deeper than the threshold depth. In FIG. 5B, the electrode pad visual display is directed to activate an LED to emit green light, or optionally no light, because the determined depth satisfies or falls within the threshold depth. In FIG. 5C, the electrode pad visual display is directed to activate an LED to emit a yellow light, red light, or some other light because the determined depth is shallower than the threshold depth. Alternatively, the colors may be otherwise set or determined to address accessibility issues such as user colorblindness.

Figure 6A:
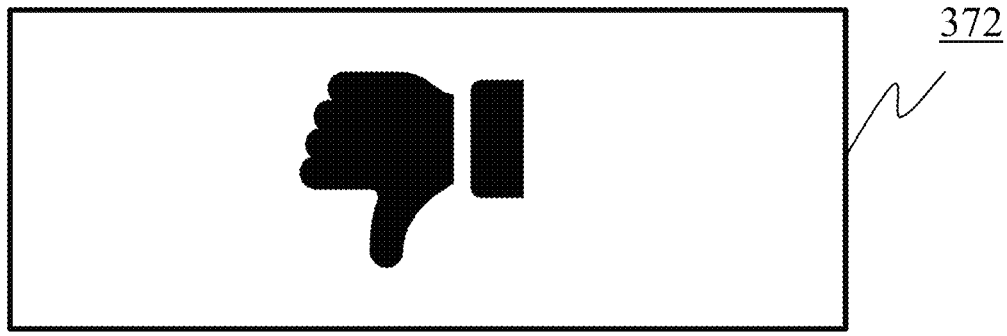
FIG. 6A is a schematic representation of an electrode pad visual display of an AED device, in accordance with an embodiment.
Figure 6B:
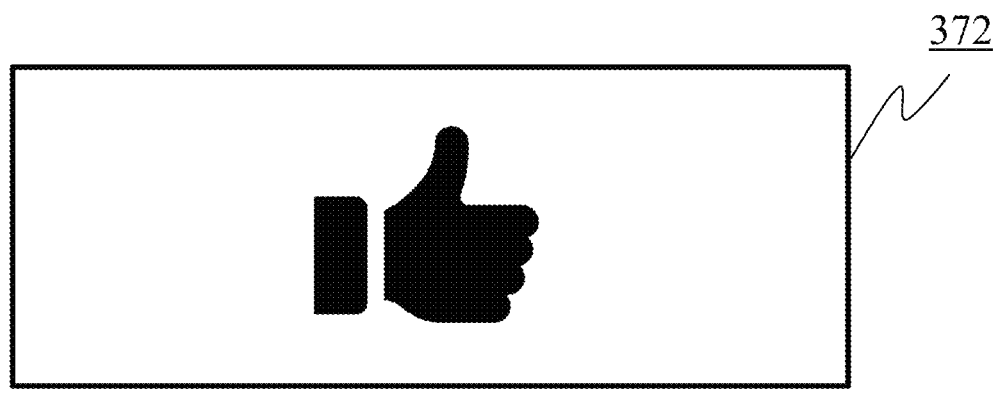
FIG. 6B is a schematic representation of an electrode pad visual display of an AED device, in accordance with an embodiment.
Figure 6C:
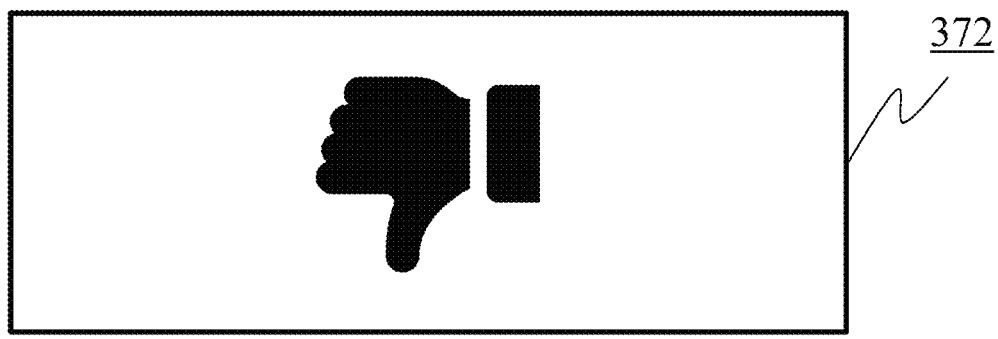
FIG. 6C is a schematic representation of an electrode pad visual display of an AED device, in accordance with an embodiment.

Referring to FIGS. 6A-6C, for example, the controller and/or the one or more electrode pad visual displays may be configured to activate, display, highlight, or otherwise activate display of an icon to provide the indicator. In FIG. 6A, the electrode pad visual display is directed to provide or display an icon such as a thumbs down icon because the determined depth is deeper than the threshold depth. In FIG. 6B, the electrode pad visual display is directed to directed to provide or display an icon such as a thumbs up icon, or optionally no icon, because the determined depth satisfies or falls within the threshold depth. In FIG. 6C, the electrode pad visual display is directed to provide or display an icon such as a thumbs down icon or other icon because the determined depth is shallower than the threshold depth. Any icons suitable to convey the necessary depth indication may be used.

Returning to method 100 in FIG. 1, at step 160 of the method the system receives and processes a signal received from a sensor to determine a rate of chest compressions provided during CPR. According to an embodiment, the signal is an electrical signal and/or an accelerometer signal, although other types of sensor signals are possible. The signal is optionally detected by a sensor in the AED device, a sensor in one or both of the electrode pads, or from some other source. The signal is a mechanical and/or electrical signal that can be analyzed or processed to determine a rate of chest compressions during CPR. According to an embodiment, impedance signals between the two or more electrode pads can be used to detect CPR-related impedance changes, including rate of CPR compressions. According to another embodiment, the chest electrode signals are analyzed to separate cardiac-related signals (e.g., electrocardiogram or ECG) and a CPR-related artifacts such as rate of CPR compressions. Many other methods are possible to analyze the mechanical and/or electrical signal detected by the AED device sensor to determine or estimate a rate of chest compressions during CPR.

According to an embodiment, the system is configured to analyze the signal after a plurality chest compressions, above or below a certain threshold. The signal can be stored in memory while being stored or after being processed. Accordingly, the determined rate can be stored in memory during or after processing.

According to an embodiment, the determined rate may be a numerical value, percentage, or other value indicating a rate. For example, the determined rate may be a measurement in inches or centimeters. Therefore, the output of step 160 of the method may be any indication of determined rate, such as 130 compressions/minute, 110 compressions/minute, 90 compressions per minute, or any other measurement.

At step 170 of the method, the AED device compares the determined rate of the chest compressions during CPR to a threshold rate. The threshold rate can be any rate determined to be sufficient to push blood throughout the victim's body enough times a minute. This rate can be determined experimentally, can be based on CPR standards, or otherwise determined. According to current standards from the American Heart Association, for example, users should provide chest compressions at a rate of 100 to 120 compressions/minute to a depth of at least 2 inches (5 cm) for an average depth. According to an embodiment, the threshold rate is pre-programmed into the AED device, such as into the controller, during manufacture or during installation. Alternatively, the threshold rate may be a setting that can be adjusted by the user during installation or before/during use of the AED device in an emergency situation.

At step 180 of the method, the AED device determines, based on the comparison, that the determined rate exceeds or falls below the threshold rate. According to an embodiment, the result of the comparison of the determined rate of the one or more chest compressions to the predetermined threshold rate can be a numerical value or simply a digital "exceeds" or "falls below" indication. There are many other ways to indicate that the determined rate exceeds or falls below the threshold rate.

For example, the comparison may result in a numerical value indicating by how much the determined rate exceeds or falls below the threshold rate. For example, as described above, possible determined rate measurements may be measurements such as 130 compressions/minute, 110 compressions/minute, 90 compressions per minute. Similarly, the threshold rate for an adult may be within the range of 100 to 120 compressions/minute. Accordingly, the three example measurements result in the following comparisons:

1. A determined rate of 130 compressions/minute compared to the threshold rate of 100 to 120 compressions/minute results in a difference of between 30 and 10 compressions/minute in excess of the threshold rate. In this example, the output of step 180 of the method is a determination by the AED device that the determined rate EXCEEDS the threshold rate. In this example, the user is compression the chest too many times a minute, which can result in ineffective CPR.

2. A determined rate of 90 compressions/minute compared to the threshold rate of 100 to 120 compressions/minute results in the determined rate falling within the threshold rate range. In this example, the output of step 180 of the method is a determination by the AED device that the determined rate neither exceeds for falls below the threshold rate.

3. A determined rate of 130 compressions/minute compared to the threshold rate of 100 to 120 compressions/minute results in a difference of between 10 and 40 compressions/minute below the threshold rate. In this example, the output of step 180 of the method is a determined by the AED device that the determined rate FALLS BELOW the threshold rate. In this example, the user is compression the chest too infrequently a minute, which can result in ineffective CPR.

Although the previous examples are shown using exact rate measurements, it should be appreciated that these are provided only as non-limiting examples. Many other methods for comparing a determined rate to a threshold rate are possible.

At step 190 of the method, the AED devices provides, via the electrode pad visual display, a rate indication to the user of the AED that the determined rate of the one or more chest compressions during CPR exceeds or falls below the threshold rate. For example, referring to FIG. 3 are first electrode pad 370*a* and second electrode pad 370*b*. One or both of the electrode pads may comprise one or more electrode pad visual displays 372. Although FIG. 3 shows both electrode pads comprising an electrode pad visual display 372, it should be appreciated that only one pad may comprise a visual display.

According to an embodiment, the controller directs the electrode pad visual display to provide rate indication to the user of the AED that the determined rate of the one or more chest compressions during CPR exceeds or falls below the threshold rate, based on the output of step 180 of the method. Returning to the non-limiting examples discussed above, the controller may take the following action in response to each of the three comparisons:

1. A determined rate of 130 compressions/minute compared to the threshold rate of 100 to 120 compressions/minute results in a difference of between 30 and 10 compressions/minute in excess of the threshold rate. In this example, the output of step 180 of the method is a determination by the AED device that the determined rate EXCEEDS the threshold rate. In this example, the controller directs the one or more electrode pad visual displays to provide an indication that the determined rate EXCEEDS the threshold rate.

2. A determined rate of 90 compressions/minute compared to the threshold rate of 100 to 120 compressions/minute results in the determined rate falling within the threshold rate range. In this example, the output of step 180 of the method is a determination by the AED device that the determined rate neither exceeds for falls below the threshold rate. In this example, the controller may provide no direction to the one or more electrode pad visual displays. Alternatively, the controller may direct the one or more electrode pad visual displays to provide an indication that the determined rate is within or otherwise satisfies the threshold rate.

3. A determined rate of 130 compressions/minute compared to the threshold rate of 100 to 120 compressions/minute results in a difference of between 10 and 40 compressions/minute below the threshold rate. In this example, the output of step 180 of the method is a determined by the AED device that the determined rate FALLS BELOW the threshold rate. In this example, the controller directs the one or more electrode pad visual displays to provide an indication that the determined rate FALLS BELOW the threshold rate.

The indication that the determined rate exceeds, meets, or falls below the threshold rate may be any indication, provided visually by the one or more electrode pad visual displays, sufficient to communicate this information to the user. Although several examples of indications provided via the one or more electrode pad visual displays are provided below, it should be understood that these are non-limiting examples.

Figure 7:
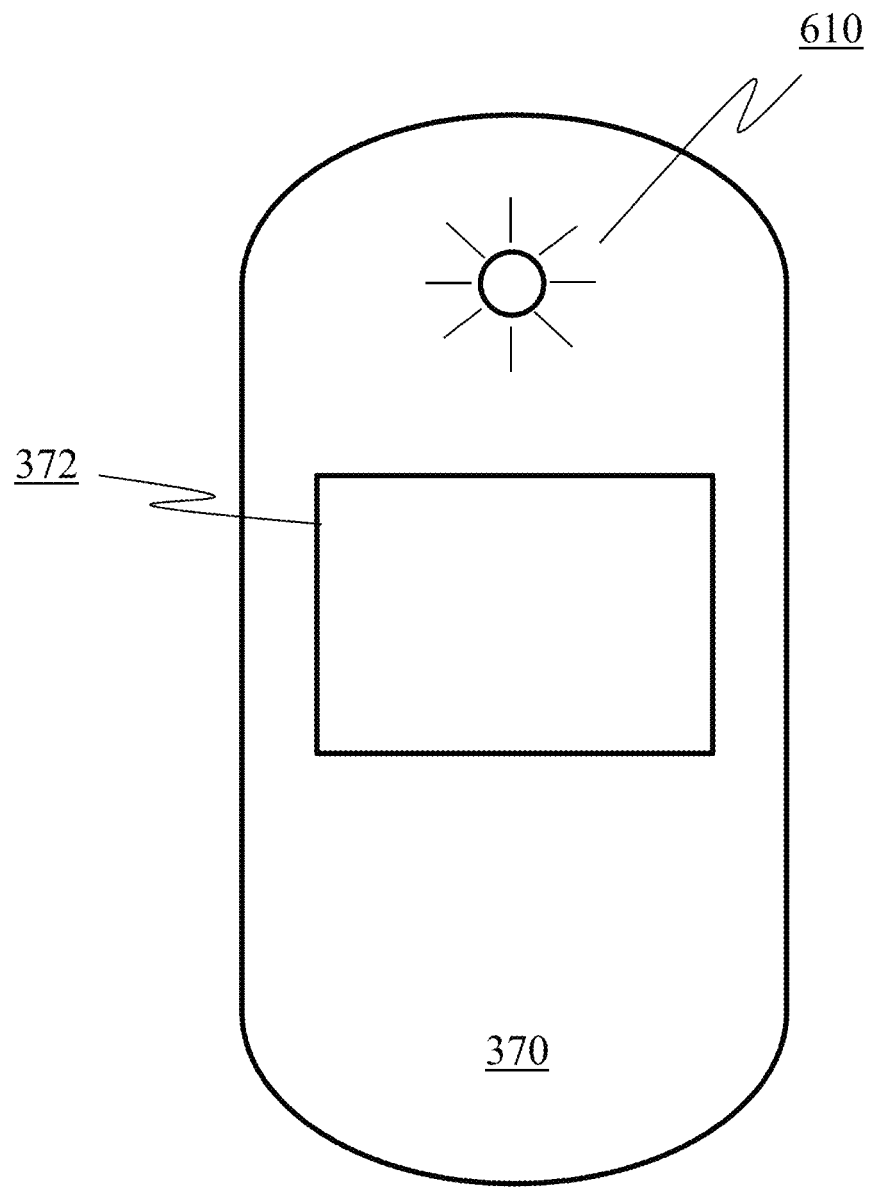
FIG. 7 is a schematic representation of an electrode pad visual display of an AED device, in accordance with an embodiment.

According to one embodiment, the one or more electrode pad visual displays may comprise a visual display such as a liquid crystal display or other graphical user interface configured to provide the indication regarding the determined depth. Referring to FIG. 7, for example, the controller and/or the one or more electrode pad visual displays may be configured to activate, display, highlight, or otherwise activate or provide an indicator such as an LED light to provide the indicator. In FIG. 7, the electrode pad visual display is directed to activate an LED 610 to emit light in a pattern or a specific color to indicate rate. For example, the LED may emit a red light if the determined rate is slower than the threshold rate, green light if the determined rate is at or within the threshold rate, and yellow light if the determined rate is faster than the threshold rate. Many other color combinations and display options are possible. For example, the LED 610 may flash at the threshold rate, thereby indicating to the user that their compressions are either slower or faster than the threshold rate. For AED devices that emit a sound at a threshold chest compression rate, the electrode pad visual display may flash or otherwise provide an indication at the same rate as the emitted sound.

According to an embodiment, the electrode pad visual display can provide the rate indication in a manner that coaches the user to increase or decrease the determined chest compression rate in order to achieve the threshold chest compression rate. The electrode pad visual display and controller can be configured to direct the electrode pad visual display to initially provide the rate indication at the determined rate rather than at the threshold rate. For example, in a case where the user is compressing the chest too slowly, the controller can direct the electrode pad visual display to initially provide the rate indication at the determined slower chest compression rate. The controller can then direct the electrode pad visual display to increase the rate indication over time until it reaches the threshold rate. The user will increase their chest compression rate to match the increasing rate of the chest compression rate indicator. For example, if the user is compression the chest at 80 compressions per minute, the LED 610 can initially indicate a rate of 80 flashes per minute. The controller than then increase the rate of flashing of the LED 610 to cause the user to match the increase rate, thereby soon reaching the threshold rate and significantly improving the victim's likelihood of survival. The same process can be utilized to slow the user from a faster chest compression rate to the threshold chest compression rate.

The rate of increase or decrease can be predetermined or can be determined based in whole or in part on the determined rate relative to the threshold rate. For example, if the chest compressions are determined to be 70 compressions per minute, the rate of increase may be much faster than a scenario where the determined chest compression rate is 95 compressions per minute.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures.

What is claimed is:

1. An automated external defibrillator (AED) for use during cardiopulmonary resuscitation (CPR), the AED comprising:
    a first electrode pad configured to obtain at least a portion of an electrocardiogram (ECG) signal from an individual;
    a second electrode pad configured to obtain at least a portion of an electrocardiogram (ECG) signal from the individual, wherein the first electrode pad and/or the second electrode pad includes an electrode pad visual display configured to be visible to a user of the AED while providing CPR to the individual; and
    a controller in communication with the first electrode pad and the second electrode pad, the controller configured to:
        (i) process an accelerometer signal received from a sensor to determine a depth of one or more chest compressions during CPR, wherein the sensor includes an accelerometer in the first electrode pad and/or in the second electrode pad;
        (ii) compare the determined depth of the one or more chest compressions during CPR to a threshold depth;
        (iii) determine, based on the comparison, that the determined depth exceeds or falls below the threshold depth; and
        (iv) direct the electrode pad visual display to provide a depth indication to the user of the AED that the determined depth of the one or more chest compressions during CPR exceeds or falls below the threshold depth.

2. The AED of claim 1, wherein the controller is further configured to:
    (i) process an electrical signal and/or an accelerometer signal received from a sensor to determine a rate of chest compressions during CPR;
    (ii) compare the determined rate of the chest compressions during CPR to a threshold rate;
    (iii) determine, based on the comparison, that the determined rate exceeds or falls below the threshold rate; and (iv) direct the electrode pad visual display to provide a rate indication to the user of the AED that the determined rate of the chest compressions during CPR exceeds or falls below the threshold rate.

3. The AED of claim 1, wherein the first electrode pad and/or in the second electrode pad is/are disposable.

4. The AED of claim 1, wherein the electrode pad visual display includes one or more LEDs configured to provide the indication to the user of the AED that the determined depth of the one or more chest compressions during CPR exceeds or falls below the threshold depth.

5. The AED of claim 1, wherein the electrode pad visual display is further configured to provide the depth indication via one or more colors, one or more words, and/or one or more icons.

6. The AED of claim 2, wherein the electrode pad visual display is further configured to provide the rate indication via one or more colors, one or more words, and/or one or more icons.

7. The AED of claim 2,
wherein the electrode pad visual display is furthrt configured to provide the rate indication via a light, and
wherein the controller is further configured to:
(i) initially direct the light to flash at the determined rate; and
(ii) subsequently direct the light to flash at a rate closer to the threshold rate.

8. The AED of claim 1, wherein both the first electrode pad and the second electrode pad include an electrode pad visual display.

9. A method for cardiopulmonary resuscitation (CPR) using an automated external defibrillator (AED), the AED comprising:
(i) a first electrode pad configured to obtain at least a portion of an electrocardiogram (ECG) signal from an individual;
(ii) a second electrode pad configured to obtain at least a portion of an electrocardiogram (ECG) signal from the individual, wherein the first electrode pad and/or the second electrode pad includes an electrode pad visual display configured to be visible to a user of the AED while providing CPR to the individual; and
(iii) a controller in communication with the first electrode pad and the second electrode pad, the method comprising:
processing an accelerometer signal received from a sensor to determine a depth of one or more chest compressions during CPR, wherein the sensor includes an accelerometer in the first electrode pad and/or in the second electrode pad;
comparing the determined depth of the one or more chest compressions during CPR to a threshold depth;
determining, based on the comparison, that the determined depth exceeds or falls below the threshold depth; and
providing, via the electrode pad visual display, a depth indication to the user of the AED that the determined depth of the one or more chest compressions during CPR exceeds or falls below the threshold depth.

10. The method of claim 9, further comprising the steps of:
processing an electrical signal and/or an accelerometer signal received from a sensor to determine a rate of chest compressions during CPR;
comparing the determined rate of the chest compressions during CPR to a threshold rate;
determining, based on the comparison, that the determined rate exceeds or falls below the threshold rate; and
providing, via the electrode pad visual display, a rate indication to the user of the AED that the determined rate of the chest compressions during CPR exceeds or falls below the threshold rate.

11. The method of claim 9, wherein the electrode pad visual display is further configured to provide the depth indication via one or more colors, one or more words, and/or one or more icons.

12. The method of claim 10, wherein the electrode pad visual display is further configured to provide the rate indication via one or more colors, one or more words, and/or one or more icons.

13. The method of claim 9, wherein both the first electrode pad and the second electrode pad include an electrode pad visual display.

* * * * *